United States Patent [19]

Reuter et al.

[11] Patent Number: 4,600,708
[45] Date of Patent: Jul. 15, 1986

[54] PROPRANOLOL HYDROCHLORIDE LIQUID FORMULATIONS

[75] Inventors: Gerald L. Reuter, Plattsburgh; Mark E. Coons, Champlain, both of N.Y.

[73] Assignee: American Home Products Corporation, New York, N.Y.

[21] Appl. No.: 757,213

[22] Filed: Jul. 19, 1985

[51] Int. Cl.⁴ ............... A61K 31/13; A61K 31/135; A61K 31/685
[52] U.S. Cl. ............................ 514/78; 514/652; 514/657
[58] Field of Search ............... 514/78, 652, 657

[56] References Cited

U.S. PATENT DOCUMENTS 3,701,666 10/1972 White ........................................ 99/1
3,920,819 11/1975 Stephens ............................. 424/181

FOREIGN PATENT DOCUMENTS 51-125719 4/1976 Japan .

Primary Examiner—Stanley J. Friedman
Attorney, Agent, or Firm—Walter Patton

[57] ABSTRACT

Therapeutic liquid oral dosage formulations of propranolol hydrochloride are provided which contain lecithin and/or a basic amino acid to impart taste masking characteristics and/or contain a basic amino acid to impart anesthesia masking characteristics.

4 Claims, No Drawings

PROPRANOLOL HYDROCHLORIDE LIQUID FORMULATIONS

BACKGROUND OF THE INVENTION

This invention relates to liquid therapeutic dosage propranolol hydrochloride formulations and more particularly relates to such therapeutic formulations containing lecithin.

Previously, propranolol hydrochloride has been difficult to formulate into liquid dosage form due to its very bitter taste and its ability to impart an anesthetic effect in the mouth.

Various approaches to this formulation problem have been considered, and the approach which appeared to us to offer the greater advantage was to formulate propranolol hydrochloride in a liquid medium containing a polymer which would reduce its unpleasant taste and mouthfeel characteristics. Acacia, polyvinylpyrolidone, xanthan, tragacanth, and gelatin were some of the polymers evaluated. Gelatin appeared to offer a taste modification advantage but it was not adequate.

DESCRIPTION OF THE INVENTION

The present invention provides a solution to this formulation problem by the use of lecithin and/or a basic amino acid to mask the bitter taste of propranolol hydrochloride and the use of a basic amino acid to mask the anesthetic effect of propranolol hydrochloride.

According to an aspect of this invention a liquid therapeutic dosage form composition is provided containing propranolol hydrochloride, lecithin and water. Levels of lecithin ranging from 1% to 20% were evaluated for their taste masking potential. Approximately 8% lecithin appeared to be the lowest level which provided acceptable taste masking characteristics at the target propranolol hydrochloride strength of 10 milligrams per milliliter. For other concentrations of propranolol hydrochloride, lower or higher lecithin concentrations will be appropriate. For example, when stability, preservative and other agents are incorporated into a formulation containing about 10 milligrams per milliliter of propranolol hydrochloride, then the lecithin content can range from about 8 to about 14 percent weight by volume of composition.

According to another aspect of this invention a liquid thereapeutic dosage form composition is provided containing propranolol hydrochloride, a basic amino acid and water. A level of 0.5% by weight of a basic amino acid provides acceptable taste masking characteristics and anesthesia masking characteristics at the target propranolol hydrochloride strength of 10 milligram per milliliter. For other concentrations of propranolol hydrochloride lower or higher basic amino acid concentrations will be appropriate. For example when stability, preservative and other agents are incorporated in a formulation containing about 10 milligrams per milliliter of propranolol hydrochloride, then the basic amino acid content can range from about 0.5 to 10% by weight of the composition.

Suitable grades of lecithin are available in various liquid and solid forms. See, for example, "Lecithin—Its Composition, Properties and Use in Cosmetic Formulations", Cometics and Perfumery, Vol. 89, July 1974, pages 31–35, incorporated herein by reference. A refined, granular oil-free lecithin such as Centrolex F marketed by Central Soya Company is preferred, and was used in the exemplified formulations.

Suitable basic amino acids for use in the compositions of this invention include L-lysine, L-arginine, DL-histadine and L-histidine.

Most preferably, the liquid therapeutic dosage forms of the present invention contain both lecithin and a basic amino acid. In addition to these two ingredients the compositions can contain additives to produce stable and effective suspensions. For example surfactants such as polysorbate 20, polysorbate 80, and polysorbate 65, manufactured by ICI America, Inc. and Emsorb 6912 brand of polyoxyethylene (20) sorbitan monoisostearate marketed by Emery Industries are suitable at a concentration of about 0.5% by weight of the composition; although concentrations as high as 1% by weight of the composition are acceptable. Surfactants with a hydrophilic-hydrophobic balance less than 12 are not considered useful.

Physical property modifiers to improve stability can also be used in the compositions of this invention including monovalent and trivalent sodium salts such as sodium benzoate, sodium citrate, sodium phosphate and sodium lactate in concentrations ranging up to 5% preferably about 0.5% by weight of the composition. Sodium lactate and sodium citrate in a 1:1 weight ratio are preferred. Another physical property modifier, i.e. viscosity enhancer, useful also to improve high temperature stability is Veegum K, a magnesium aluminum silicate, USP, which can be added at levels of about 0.1 to 0.5% by weight of the composition. Preservatives can be added such as methyl paraben, propyl paraben, sodium benzoate and mixures thereof. An oxygen or halogen based sanitizer such as monochloramine solution can also be added.

Flavorings which are in the form of an oil or which employ an oil vehicle appear to interfere with a satisfactory lecithin suspension. Such flavorings as peppermint, spearmint, cinnamon, peanut and orange are not satisfactory. Artificial raspberry and lemon flavors are satisfactory as are natural lemon and creme vanilla. Also sugar appears to have a negative effect on physical stability of the composition but saccharin sources are satisfactory.

EXAMPLE I

A formulation of the present invention was prepared having the following composition:

| Ingredient | Amount |
| --- | --- |
| Propranolol HCl | 10.0 grams |
| Lecithin Oil Free | 110.0 grams |
| Polysorbate 20 | 5.0 grams |
| Methylparaben, NF | 2.0 grams |
| Propylparaben, NF | 0.2 grams |
| Sodium Benzoate, NF | 5.0 grams |
| L-Histidine, Free Base | 5.0 grams |
| Sodium Saccharin, USP | 0.4 grams |
| Saccharin, NF | 0.4 grams |
| Simethicone, USP | 2.0 grams |
| Sodium Citrate, USP Hydrous | 12.0 grams |
| Sodium Lactate Soln, USP 60% | 20.0 grams |
| Flavor, Artificial Rasp. #19822 | 5.71 grams |
| Flavor, Natural and Artificial Lemon Juice, #5532 | 2.04 grams |
| Veegum K | 5.0 grams |
| FD & C Red #40 | 0.11 grams |
| Monochloramine Soln | QS 100 PPM |
| Purified Water | QS 1000.0 ml = |

| Ingredient | Amount |
|---|---|
| -continued | |
| Total | 1029.0 grams |

The order of addition of the various ingredients to provide the palatable, stable, oral liquid dosage form of propranolol hydrochloride compositions of this invention is critical. The composition of this Example I was prepared in the following step sequence.

Step 1: Place 550 grams of purified water into a suitable stainless steel container equipped with either a propeller or dispersator type mixer, and heat to 75°–85° C.

Step 2: Add to the contents in the container in Step No. 1 the following ingredients and mix until dissolved:
A. Methylparaben
B. Propylparaben
C. Sodium Benzoate Step 3: Cool to room temperature, and mix until clear.

Step 4: Add the lecithin slowly to the contents of the container in Step No. 3 and mix for approximately 90 minutes or until completely hydrated.

Step 5: In a separate container equipped with a mixer, add 150 ml of water and heat to 60°–70° C.

Step 6: Add to the contents of Step No. 5 the following ingredients and mix each until well dispersed:
A. Propranolol HCl
B. Sodium Citrate
C. Sodium Saccharin
D. L-Histidine
E. Polysorbate 20

Step 7: Cool the mixture in Step No. 6 to room temperature, then add the sodium lactate and mix until homogeneous.

Step 8: Slowly and continously add the mixture from Step No. 7 to the mixture of Step No. 4 and mix for 30 minutes.

Step 9: Add saccharin NF and mix.

Step 10: Add simethicone and mix until homogeneous.

Step 11: Add Red #40 and flavor agents, then mix until homogeneous.

Step 12: Into a separate container equipped with a mixer, place 80 ml of purified water and heat to 85°–95° C.

Step 13: Add to the container in Step No. 12 the Veegum K and mix at high speed until completely hydrated (approximately 30 minutes).

Step 14: Cool to room temperature, then add to the container in Step No. 11 and mix until uniform.

Step 15: Add monochloramine solution to yield 100 ppm.

Step 16: QS to final volume using purified water and mix well to make homogeneous.

Step 17: Homogenize the suspension at a pressure about 500–1500 psi.

Additional exemplifications of the compositions of this invention appear in Table 1 wherein the order of admixture of ingredients was generally the same as above.

TABLE I

| | Example 2 | Example 3 | Example 4 | Example 5 | Example 6 |
|---|---|---|---|---|---|
| Propranolol HCL | 10 g | 10 g | 10 g | 10 g | 10 g |
| Lecithin, Oil Free | 110 g | 110 g | 110 g | 110 g | 110 g |
| Polysorbate 20 | 5.0 g | 5.0 g | 5.0 g | 5.0 g | 5.0 g |
| Methyl paraben | 1.8 g | 2.0 g | 2.0 g | 2.0 g | 1.8 g |
| Propyl paraben | 0.2 g | 0.2 g | 0.2 g | 0.2 g | 0.2 g |
| Butyl paraben | 0.2 g | — | — | — | 0.2 g |
| Sodium Benzoate | — | 2.5 g | 5.0 g | 5.0 g | — |
| L-Arginine Free Base | — | 5.0 g | — | — | — |
| L-Histidine-HCl | — | 5.0 g | — | — | — |
| L-Histidne Free Base | — | — | 5.0 g | 5.0 g | — |
| Sodium Saccharin, USP | 0.3 g | 0.6 g | 0.6 g | 0.4 g | 0.3 g |
| Saccharin NF | — | — | — | 0.4 g | — |
| Simethicone, USP | 2.0 g | 2.0 g | 3.0 g | 2.0 g | 2.0 g |
| Sodium Citrate, USP hydrous | 12.0 g | 12.0 g | 12.0 g | 12.0 g | 12.0 g |
| Sodium Lactate Soln USP 60% | 20.0 g | 20.0 g | 20.0 g | 20.0 g | 20.0 g |
| Veegum K | — | — | — | 5.0 g | — |
| FD & C Red #40 | — | — | — | 0.11 g | — |
| Flavor, Creme Vanilla | — | 0.93 ml | 0.93 ml | — | — |
| Flavor, Nat. & Art. Lemon Juice | — | 1.15 ml | 1.15 ml | 2.04 ml | — |
| Flavor, Art. Raspberry | — | — | — | 5.71 ml | — |
| D-Aspartic Acid | | | | | |
| Xylose | | | | | |
| Glycerin USP | | | | | |
| Purified Water, USP | QS 1000 mls | QS 1000 ml | QS 1000 mls | QS 1000 mls | QS 1000 mls |

| | Example 7 | Example 8 | Example 9 | Example 10 |
|---|---|---|---|---|
| Propanolol HCL | 10 g | 10 g | 10 g | 10 g |
| Lecithin, Oil Free | 110 g | 110 g | 110 g | — |
| Polysorbate 20 | 5.0 g | 5.0 g | 5.0 g | — |
| Methyl paraben | 2.0 g | 2.0 g | 2.0 g | 1.8 g |
| Propyl paraben | 0.2 g | 0.2 g | 0.2 g | 0.2 g |
| Butyl paraben | — | — | — | — |
| Sodium Benzoate | 2.5 g | 5.0 g | 5.0 g | — |
| L-Arginine Free Base | 5.0 g | — | — | 21 g |
| L-Histidine-HCl | 5.0 g | — | — | 10 g |
| L-Histidne Free Base | — | 5.0 g | 5.0 g | — |
| Sodium Saccharin, USP | 0.6 g | 0.6 g | 0.4 g | — |
| Saccharin NF | — | — | 0.4 g | — |
| Simethicone, USP | 2.0 g | 3.0 g | 2.0 g | — |
| Sodium Citrate, USP hydrous | 12.0 g | 12.0 g | 12.0 g | — |
| Sodium Lactate Soln USP 60% | 20.0 g | 20.0 g | 20.0 g | — |
| Veegum K | — | — | 5.0 g | — |

TABLE I-continued

| | | | | |
|---|---|---|---|---|
| FD & C Red #40 | — | — | 0.11 g | — |
| Flavor, Creme Vanilla | 0.93 ml | 0.93 ml | — | — |
| Flavor, Nat. & Art. Lemon Juice | 1.15 ml | 1.15 ml | 2.04 ml | — |
| Flavor, Art. Raspberry | — | — | 5.71 ml | — |
| D-Aspartic Acid | — | — | — | 8 g |
| Xylose | — | — | — | 200 g |
| Glycerin USP | — | — | — | 50 g |
| Purified Water, USP | QS 1000 ml | QS 1000 ml | QS 1000 ml | QS 1000 ml |

We claim:

1. A liquid oral therapeutic dosage form composition of propranolol hydrochloride having satisfactory taste and anesthesia masking characteristics containing for each 10 milligrams per milliliter of propranolol hydrochloride in such composition about 8 to about 14 precent weight by volume of oil free lecithin and about 0.5 to 10% by weight of at least one basic amino acid.

2. The liquid oral therapeutic dosage form of claim 1 wherein the basic amino acid is L-histidine free base.

3. The liquid oral therapeutic dosage form of claim 1 wherein the basic amino acids are L-arginine free base and L-histidine HCl.

4. The liquid oral therapeutic dosage form of claim 1 wherein the basic amino acids are L-arginine, free base and L-histidine HCl.

* * * * *